(12) United States Patent
Yasui (10) Patent No.: US 10,316,470 B2
(45) Date of Patent: Jun. 11, 2019

(54) TISSUE PAPER

(71) Applicant: Daio Paper Corporation, Ehime (JP)

(72) Inventor: Shuta Yasui, Shizuoka (JP)

(73) Assignee: Daio Paper Corporation, Ehime (JP)

( * ) Notice: Subject to any disclaimer, the term of this patent is extended or adjusted under 35 U.S.C. 154(b) by 0 days.

(21) Appl. No.: 15/549,885

(22) PCT Filed: Mar. 15, 2016

(86) PCT No.: PCT/JP2016/058148
§ 371 (c)(1),
(2) Date: Aug. 9, 2017

(87) PCT Pub. No.: WO2016/158385
PCT Pub. Date: Oct. 6, 2016

(65) Prior Publication Data
US 2018/0023255 A1 Jan. 25, 2018

(30) Foreign Application Priority Data
Mar. 31, 2015 (JP) .................................. 2015-074102

(51) Int. Cl.
| | |
|---|---|
| *A61K 9/70* | (2006.01) |
| *D21H 27/00* | (2006.01) |
| *A47K 7/00* | (2006.01) |
| *A47K 10/16* | (2006.01) |
| *D21H 27/30* | (2006.01) |
| *D21H 17/06* | (2006.01) |
| *A61K 8/02* | (2006.01) |
| *A61K 8/37* | (2006.01) |

(52) U.S. Cl.
CPC ............. *D21H 27/008* (2013.01); *A47K 7/00* (2013.01); *A47K 10/16* (2013.01); *A61K 8/0208* (2013.01); *A61K 8/37* (2013.01); *D21H 17/06* (2013.01); *D21H 27/00* (2013.01); *D21H 27/002* (2013.01); *D21H 27/30* (2013.01)

(58) Field of Classification Search
None
See application file for complete search history.

(56) References Cited

U.S. PATENT DOCUMENTS

2009/0297586 A1* 12/2009 Shannon .............. D21H 27/002
424/443

FOREIGN PATENT DOCUMENTS

| JP | H02-74694 A | 3/1990 |
| JP | 2011-152426 A | 8/2011 |
| JP | 2011-206189 | 10/2011 |
| JP | 2013-511509 A | 4/2013 |
| JP | 2013-511626 A | 4/2013 |

* cited by examiner

*Primary Examiner* — Susan T Tran
(74) *Attorney, Agent, or Firm* — Muncy, Geissler, Olds & Lowe, P.C.

(57) ABSTRACT

To provide tissue paper with an excellent "moist texture" and high "smooth texture."
2-ply tissue paper is characterized by the basis weight per ply being 15 to 18 g/m², the 2-ply paper thickness being 135 to 160 μm, and containing 2.9 g/m² or more and 8.0 g/m² or less of chemical agent which contains glycerin and 1,3-propanediol in a total amount of 83.7 mass % or more, wherein the mass ratio of glycerin and 1,3-propanediol is 1:0.04 or more and 1:5.58 or less.

3 Claims, 2 Drawing Sheets

TISSUE PAPER

TECHNICAL FIELD

The present invention relates to tissue paper, particularly tissue paper containing a moisturizer.

BACKGROUND ART

Tissue paper can be roughly classified into lotion tissue paper in which a moisturizer is contained in tissue base paper after papermaking, moisturizing tissue paper called e.g. chemicals applied type, a general-purpose type which does not contain a moisturizer, and non-moisturizing tissue paper called e.g. a general type.

Moisturizing tissue paper is used mainly to directly touch the skin, for example blowing nose and removing makeup, and is particularly required to have a good texture to the skin during use.

Incidentally, the quality characteristics of tissue paper include mainly "soft texture," "smooth texture," a "moist texture," a "sticky texture," a "thick texture" and "toughness (strength•a relief feeling)."

The moisturizing tissue paper is more excellent in "soft texture," "smooth texture" and a "moist texture" due to the effect of a moisturizer than those of the non-moisturizing tissue paper; however, there are no conventional moisturizing tissue paper in which particularly both "smooth texture" and a "moist texture" are satisfied at a high level. In addition, users require further improvement of good texture to the skin; however, it is very difficult to improve both "smooth texture" and a "moist texture."

That is, in conventional moisturizing tissue paper, "soft texture" and a "moist texture," are improved by raising water retention properties in paper because of the moisture absorption action of the moisturizer. With this change, "smooth texture" can be felt, too. However, in the case of conventional moisturizers, for example, when increasing the content thereof, a "moist texture" is increased, and simultaneously a "sticky texture" is also increased. Following this, the "smooth texture" on the surface is reduced and is not easily felt. In addition, containing excessive moisturizer can be a factor of lowering resilience of paper, and this can be a factor of not feeling "smooth texture" easily.

CITATION LIST

Patent Literature

Patent Literature 1: JP 2013-511509 A
Patent Literature 2: JP 2013-511626 A
Patent Literature 3: JP 2-74694 A

SUMMARY OF THE INVENTION

Technical Problem

Therefore, a main subject of the present invention is to provide moisturizing tissue paper, in which particularly both a "moist texture" and "smooth texture" are improved, a "moist texture" which conventional moisturizing tissue paper do not have is retained, and simultaneously "smooth texture" can be sufficiently felt.

Solution to Problem

The means for solving the above problem and their operational advantage are as described below.

[Invention Described in Claim 1]
2-ply tissue paper, wherein
a basis weight per ply is 15 to 18 g/m², the 2-ply paper thickness is 135 to 160 μm, and the 2-ply tissue paper containing
2.9 g/m² or more and 8.0 g/m² or less of chemical agent which contains glycerin and 1,3-propanediol in a total amount of 83.7 mass % or more, wherein the mass ratio of glycerin and 1,3-propanediol is above 1:0.04 and 1:5.58 or less.

[Invention Described in Claim 2]
The 2-ply tissue paper, wherein
a basis weight per ply is 16.2 g/m² or more and 17.4 g/m² or less,
the 2-ply paper thickness is 136 μm or more and 156 μm or less, and the 2-ply tissue paper containing
2.9 g/m² or more and 8.0 g/m² or less of chemical agent which contains glycerin and 1,3-propanediol in a total amount of 83.7 mass % or more, wherein the mass ratio of glycerin and 1,3-propanediol is above 1:0.04 and 1:5.58 or less.

[Invention Described in Claim 3]
The 2-ply tissue paper according to claim 1 or 2, wherein
the 2-ply dry tensile strength in the CD direction is 51 cN/25 mm or more and 62 cN/25 mm or less,
the 2-ply wet tensile strength in the CD direction is 39 cN/25 mm or more and 58 cN/25 mm or less, and
the ratio of the 2-ply wet tensile strength in the CD direction to the 2-ply dry tensile strength in the CD direction is 0.68 or more.

Advantageous Effects of Invention

The present inventors investigated the selection of various chemical agents, the blending ratio and the physical properties of paper for the purpose of obtaining both a "moist texture" and "smooth texture" in moisturizing tissue paper, thereby completing the tissue paper according to the present invention.

According to the present invention, when in 2-ply tissue paper, the basis weight per ply is 15 to 18 g/m², the basis weight per ply is preferably above 16.2 g/m² and less than 17.4 g/m², the 2-ply paper thickness is 135 to 160 μm, the 2-ply paper thickness is preferably 136 μm or more and 156 μm or less, and 2.9 g/m² or more and 8.0 g/m² or less of chemical agent, which contains particularly glycerin and 1,3-propanediol in a total amount of 83.7 mass % or more, wherein the mass ratio of glycerin and 1,3-propanediol (the mass ratio of 1,3-propanediol to 1 glycerin) is above 1:0.04 and 1:5.58 or less, is contained, both a "moist texture" and "smooth texture" are obtained at a very high level compared to those of conventional moisturizing tissue paper. Furthermore, a "sticky texture" is limited and "soft texture" is also high. As described above, according to the present invention, the quality characteristics of tissue paper, "soft texture," "smooth texture," a "moist texture" and a "sticky texture" are excellent. The above effects will be described particularly in examples described below.

In this case, it is desirable that the 2-ply dry tensile strength in the CD direction be 51 cN/25 mm or more and 62 cN/25 mm or less, the 2-ply wet tensile strength in the CD direction be 39 cN/25 mm or more and 58 cN/25 mm or less, and the ratio of the 2-ply wet tensile strength in the CD direction to the 2-ply dry tensile strength in the CD direction be 0.68 or more. By adjusting the dry tensile strength to such range, strength which can withstand use is secured, and simultaneously a decrease in wet strength by containing chemical agent is suppressed, and strength can be secured for example even when in use with wet hands.

DESCRIPTION OF EMBODIMENTS

Embodiments of the present invention will now be described.

The tissue paper according to the embodiment is 2-ply tissue paper which has a relatively high basis weight, wherein the basis weight per ply is 15 to 18 g/m$^2$, the basis weight per ply is preferably 16.82 g/m$^2$ or more and 17.4 g/m$^2$ or less, and further preferably 11.0 g/m$^2$ or more and 12.5 g/m$^2$ or less, the 2-ply paper thickness is 135 to 160 μm, the 2-ply paper thickness is preferably 136 μm or more and 156 μm or less.

This tissue paper has a relatively high basis weight and has a thick texture in the paper thickness. The tissue paper has such basis weight and paper thickness, and thus in relation to this, particularly a "moist texture" and "smooth texture" are felt in combination with a peculiar moisturizer and the amount of moisturizer applied. It should be noted that the basis weight is a value measured based on JIS P 8124 (1998). In addition, as a method for measuring paper thickness, a test piece is sufficiently conditioned under the condition of JIS P 8111 (1998) and the paper thickness in a 2-ply state is then measured under the same condition using a dial thickness gauge (thickness meter) "PEACOCK G" (manufactured by OZAKI MFG. CO., LTD.) More particularly, after confirming that there are not dust etc. between the plunger and the measurement stand, the plunger is put down on the measurement stand and the scale of the dial thickness gauge is shifted for zero point adjustment. Subsequently, the plunger is put up and a sample is put on the test stand. The plunger is slowly put down and a gauge is read. At this time, the plunger is just put on. The terminal of the plunger is made of metal and a round flat surface with a diameter of 10 mm is vertically put on the flat surface of paper, and a load is about 70 gf at the time of measuring paper thickness. It should be noted that the paper thickness is an average value obtained by repeating measurement ten times.

In the meantime, the tissue paper according to the embodiment contains 2.9 g/m$^2$ or more and 8.0 g/m$^2$ or less of chemical agent which contains glycerin and 1,3-propanediol in a total amount of 83.7 mass % or more, wherein the mass ratio of glycerin and 1,3-propanediol (the mass ratio of 1,3-propanediol to 1 glycerin) is above 1:0.04 and 1:5.58 or less. When the total amount of glycerin and 1,3-propanediol is less than 83.7 mass %, both a "moist texture" and "smooth texture" are not sufficiently improved. Besides, when the mass ratio of glycerin and 1,3-propanediol is outside a range of above 1:0.04 and 1:5.58 or less, both or either one of a "moist texture" and "smooth texture" is not easily felt. When the content of moisturizer is 2.9 g/m$^2$ or less, both a "moist texture" and "smooth texture" are not felt, and when the content is 9.2 g/m$^2$ or more, costs increase and furthermore "smooth texture" and also a "moist texture" are not easily felt.

On the other hand, fiber materials constituting the tissue paper according to the embodiment are pulp fibers and are desirably NBKP and LBKP which are used for tissue paper. Used paper pulp can be blended, but it is preferred that the tissue paper be constituted from only NBKP and LBKP, virgin pulp. The blending proportion is desirably NBKP: LBKP=25:75 to 40:60 by mass ratio. In this range, the paper strength and "soft texture" are easily expressed.

In the tissue paper according to the embodiment, it is desired that the 2-ply dry tensile strength in the CD direction be 51 cN/25 mm or more and 62 cN/25 mm or less, the 2-ply wet tensile strength in the CD direction be 39 cN/25 mm or more and 58 cN/25 mm or less, and the ratio of the 2-ply wet tensile strength in the CD direction to the 2-ply dry tensile strength in the CD direction be 0.68 or more. The dry tensile strength is prescribed in JIS P 8113 and the wet tensile strength is prescribed in JIS P 8135 (1998). This tissue paper has each strength described above, and thus the strength enough to withstand use can be shown, and "toughness (strength•a relief feeling)" is also provided for users. In the tissue paper according to the embodiment, the ratio of the 2-ply wet tensile strength in the CD direction to the 2-ply dry tensile strength in the CD direction is 0.68 or more, and a difference in strength between a dry state and a wet state is relatively small compared to that of a general moisturizing tissue. This can be easily achieved by providing the basis weight and the like and the characteristic moisturizer composition of the tissue paper according to the embodiment, and by such difference in strength, users feel "toughness (strength•a relief feeling) in the changing mode of use from a dry state to a wet state, for example particularly when blowing nose. Furthermore, a change in paper strength in such mode of use is not easily felt, and an uncomfortable feeling that "smooth texture" is changed during use is also not felt.

In order to provide the moisturizer composition of the tissue paper according to the embodiment, when adjusting the dry tensile strength and wet tensile strength to the above values, a dry paper strengthening agent and a wet paper strengthening agent can be internally added to paper materials or a wet paper web. As dry paper strengthening agents, starch, polyacrylamide, CMC (carboxymethylcellulose) or salts thereof, sodium carboxymethylcellulose, calcium carboxymethylcellulose and zinc carboxymethylcellulose and the like can be used. As wet paper strengthening agents, polyamide polyamine-epichlorohydrin resin, urea resin, acid colloid melamine resin, thermal crosslinking-coated PAM and the like can be used. It should be noted, when internally adding a dry paper strengthening agent, the amount added to pulp slurry is about 0.5 to 1.0 kg/t by weight ratio. In addition, it is desired that a wet paper strengthening agent be a cationic one, and the amount added to pulp slurry is about 5.0 to 20.0 kg/pulp t by weight ratio.

Herein, the tissue paper according to the embodiment can be produced by the same method as for a conventional moisturizing tissue. That is, single layer tissue base paper with crepe after papermaking in papermaking equipment is wound to form a primary paper roll, and two of this primary paper roll are set to laminating equipment also called a ply machine. A continuous single layer sheet is drawn out from each primary paper roll and laminated, and for example the laminated sheet is then suitably slit to wind a secondary paper roll. Using this secondary paper roll, a laminated bundle is formed in e.g. folding equipment also called inter folder, and for example cut into suitable sizes to manufacture tissue paper products. The step for applying chemicals is separately provided in any step or between steps in a series of production steps for manufacturing a product to apply a moisturizing chemicals containing a moisturizer to tissue paper, and the tissue paper according to the embodiment can be produced thereby.

The moisturizing chemicals according to the embodiment can be adjusted so that glycerin and 1,3-propanediol will be contained in a total amount of 83.7 mass % or more in active ingredients and the mass ratio of glycerin and 1,3-propanediol will be above 1:0.04 and 1:5.58 or less. More particularly, the above active ingredients are a basis, and moisturizing chemicals are adjusted to a viscosity according to an application method suitably using a solvent such as water. Other known auxiliary agents can be added to moisturizing chemicals without inhibiting the effects of glycerin and 1,3-propanediol. Naturally, these auxiliary agents in moisturizing chemicals are contained in tissue paper after applied and can constitute chemical agent. Examples of auxiliary agents include auxiliary moisturizing components such as sorbitol, hydrophilic polymer gelling agents to increase moisture retention properties in tissue paper such as glucomannan, softness improvers such as surface active agents and phosphate esters, oily components to aid the expression of smoothness such as liquid paraffin, and besides emulsifiers to improve the stabilization and application properties of a moisturizer, preservatives, defoamers and the like. These auxiliary agents can be contained as an active ingredient (absolute dry) up to a total of less than 16.3 mass %.

Moisturizing chemicals are applied to tissue base paper by external addition using known chemicals applying equipment e.g. roll transfer devices such as a flexographic press and a gravure printing machine, and a spray applicator. Moisturizing chemicals can be applied to tissue base paper from a direction, but it is desirable to apply moisturizing chemicals to both sides because smoothness on both sides is easily made even. In addition, the amount of moisturizing chemicals applied to the tissue base paper is suitably adjusted considering vaporization of water, a solvent, in the production process and the elongation of tissue base paper generated in the production process. With respect to elongation, because the tissue base paper is crepe paper having crepe, when after applying moisturizing chemicals, the winding step and folding step are carried out after the application of the moisturizing chemicals, tissue base paper is elongated, and there is a tendency that the amount applied is slightly reduced. Therefore, it is desirable that the amount of active ingredient applied be adjusted to be slightly more than a desired application amount considering elongation in such production steps.

The tissue paper according to the embodiment described above and furthermore the effects thereof particularly will be described in "Examples."

EXAMPLES

Test samples of the tissue paper according to the present invention and tissue paper different from the tissue paper of the present invention were made and investigated by a sensory test described below about the evaluation items of "soft texture," "smooth texture," "moist texture" and "sticky texture." In addition, the physical property values and composition values of each sample were measured as follows. The physical property values and composition values and test results of each sample are as shown in Tables 1 and 2 below.

[Basis Weight]

The basis weight was measured in accordance with JIS P 8124 (1998). The values in tables are the average value of each ply.

[Paper Thickness]

The paper thickness was measured in accordance with the method for measuring thickness described above under the condition of JIS P 8111 (1998) using a dial thickness gauge (thickness meter) "PEACOCK G" (manufactured by OZAKI MFG. CO., LTD.)

[Density]

The density is a value obtained by dividing a value (C) obtained by doubling the basis weight of tissue paper conditioned under the condition of JIS P 8111 (1998) by the paper thickness of tissue paper (2 ply) (D) described above, and was represented using a unit $g/cm^3$ and the third decimal place.

[Dry Tensile Strength]

The dry tensile strength was measured in accordance with the tensile test of JIS P 8113 (1998).

[Wet Tensile Strength]

The wet tensile strength was measured in accordance with the tensile test of JIS P 8135 (1998).

[Elongation Rate]

The elongation rate was measured in accordance with the tensile test of JIS P 8113 (1998) using a "universal tensile and compression testing machine TG-200N" manufactured by Minebea Co., Ltd.

[Softness]

Softness was measured in accordance with Handle-O-Meter method according to JIS L 1096 E method. It should be noted that the size of test piece was 100 mm×100 mm and clearance was 5 mm. The longitudinal direction and lateral direction of 1 ply were measured 5 times each and the average value of 10 times in total was represented using a unit of cN/100 mm.

[MMD]

This MMD is the mean deviation of coefficient of static friction and one of the indices of smoothness. A smaller value indicates higher smoothness, and a larger value indicates poorer smoothness. As a method for measuring MMD, while the contact surface of a friction block is brought into contact with the surface of a measurement sample to which 20 g/cm tension is applied in a predetermined direction at a contact pressure of 25 g, the friction block is moved by 2 cm at a speed of 0.1 cm/s in a direction almost the same as the direction in which tension is applied, and a friction coefficient at this time is measured using a friction tester KES-SE (manufactured by KATO TECH CO., LTD.) A value obtained by dividing the friction coefficient by a friction distance (travel distance=2 cm) is MMD. It should be noted that a friction block is constituted by put 20 piano wires P with a diameter of 0.5 mm side by side, and has a contact surface formed thereon so that both length and width are 10 mm. The end of the contact surface is formed with unit bulge portions of 20 piano wires P (the radius of curvature 0.25 mm).

[Product Water Content Rate]

A sample was conditioned under the condition of JIS P 8111 (1998) and the water content rate was then measured in accordance with JIS P 8127 (1998).

[Content Rate of Chemical Agent and Content of Chemical Agent]

The content rate of chemical agent and the content of chemical agent can be calculated from the measurement and calculation of a sample in the following (1) to (4), and the values in tables are values based on the measurement of samples. It should be noted that the content rate of chemical agent and the content of chemical agent can be calculated based on the composition of moisturizing chemicals and the physical properties of base paper.

(1) Measurement of Basis Weight of Sample

Tissue paper is conditioned under an environment of 23° C. and 50% R.H. prescribed in JIS P 8111 (1998). The length dimension and the width dimension of 5 pairs of tissue paper are measured to calculate tissue paper area (which is an area viewed from a view point on a line perpendicular to the flat surface of a plied sheet, and is not the total area of plied sheets and both sides thereof). Next a sample is put into a weighing bottle and dried under the drying condition at a temperature of 80° C. for 120 minutes. The weighing bottle is capped and heat is released in a desiccator, and the absolute dry mass of a pair of tissue paper (2 sheets) is found. From the absolute dry mass and the area measured above, the absolute dry basis weight (per sheet) of 5 pairs each is calculated, and the average value is used as the absolute dry basis weight ($g/m^2$) of a sample.

(2) Chemical Agent Attached Rate

Into a cylindrical weighing bottle, about 10 g of sample is put and absolutely dried by drying at 80° C. for 120 minutes. After that, the weighing bottle is capped and heat is released in a desiccator, and the absolute dry mass of a sample is found. A cylindrical filter paper filled with the sample is put into a Soxhlet extractor, and 120 to 140 mL of acetone:ethyl alcohol mixed solvent (mixed volume ratio 1:1) is put into a flat bottom flask, which is heated for 4 hours to an extent that a light boiling of the extracted liquid is maintained on a hot water bath. After heating, the extracted liquid is collected into the flask. A bent distillation tube and a condenser are set to the flask, which is heated on a hot water bath to remove the solvent. Furthermore, the flask is left to stand in a constant temperature dryer at a temperature of 105±2° C. for 90 minutes to completely remove the solvent. The mass of extract (B) (g) is found by subtracting a constant weight of the mass of the flask from the mass of flask after removing the solvent. Next, chemical agent attached rate is found by the following formula.

Chemical agent Attached Rate=[(Mass of Extract)/{(Absolute Dry Mass of Sample)−(Mass of Extract)}]×100

It should be noted that the amount and the mass ratio of glycerin and 1,3-propanediol contained in an extract can be measured by e.g. gas chromatography and mass spectroscopy (GC-MS) and high performance liquid chromatography (HPLC).

(3) Calculation of Content of Chemical Agent

The content of chemical agent is calculated by the following formula.

Content of Chemical agent ($g/m^2$)=(Absolute Dry Basis Weight calculated in (1) above)×(Number of Plies)×(Chemical agent Attached Rate calculated in (2) above)/[100+(Chemical agent Attached Rate calculated in (2) above)]

(4) [Content Rate of Chemical Agent Contained (Absolute Dry)]

The content rate of chemical agent (absolute dry) is calculated from the mass of tissue paper conditioned under the condition of JIS P 8111 (A) (g) and the mass of an extract found in (2) above (B) (g) by the following formula. Content rate of Chemical agent Contained (mass %)=(B)/(A)×100 (mass %)

It should be noted that the content rate of chemical agent can be also calculated from the mass of tissue paper (A) (g) and the ratio of solid matter obtained by removing water in chemicals.

[Sensory Test]

Sensory properties of "soft texture," "smooth texture," "moist texture" and "sticky texture" of each sample were evaluated by 30 evaluators using "5" for one with a feeling of "very excellent" compared to a reference sample, "4" for one with a feeling of "excellent," "3" for one with a feeling of "equal to the reference," "2" for one with a feeling of "poor," and "1" for one with a feeling of "sufficiently poor." The calculated average point of the evaluators was used as an evaluation value. It should be noted that "comprehensive evaluation" was made using "5" for one with a feeling of "a good texture to the skin and very high purchase intension," "4" for one with a feeling of "a good texture to the skin and high purchase intension," "3" for one with a feeling of "a normal texture to the skin and neither high nor low purchase intension," "2" for one with a feeling of "a poor texture to the skin and low purchase intension," and "1" for one with a feeling of "a very poor texture to the skin and almost no purchase intension." The calculated average point of the evaluators was used as an evaluation value.

[Test Results]

[Table 1]

Table 1 shows the test results of each sample in which the amount of 1,3-propanediol blended in chemical agent and, in relation to this, the proportion with glycerin were changed under the condition that the papermaking condition of base paper and the amount of chemicals applied and the like are fixed. The reference sample of sensory evaluation is one in which 1,3-propanediol is not contained and glycerin is a main component (Comparative Example 1). In addition, the graph of the sensory evaluation results is shown in FIG. 1.

Figure 1:
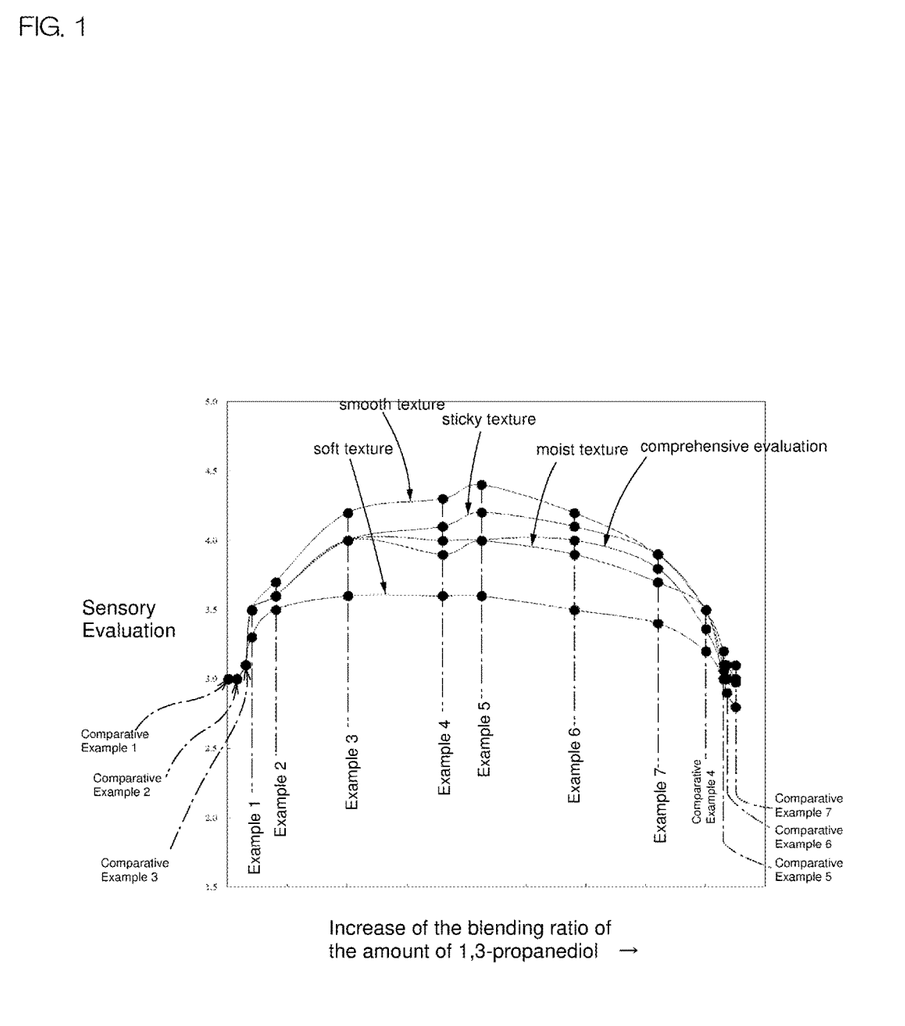
FIG. 1 is a graph showing the results of test examples according to an embodiment.

As shown in Table 1 and FIG. 1, when the mass ratio of glycerin and 1,3-propanediol is in the range of the present invention, remarkably excellent results were obtained in the evaluation items of "soft texture," "smooth texture," "thick texture," "moist texture," "sticky texture" and "comprehensive evaluation" compared to those of the reference sample. Very remarkably high evaluation was obtained particularly in "smooth texture," "moist texture" and "sticky texture." From the above, it is found that when the mass ratio of glycerin and 1,3-propanediol is in the range of the present invention, tissue paper which is "smooth and moist" and in which "stickiness" is not easily felt can be obtained. The evaluation of "soft texture" was also high.

Furthermore, it can be verified that from this Table 1, even when the content of chemical agent is in the range of the present invention, the evaluation is not good when the mass ratio of glycerin and 1,3-propanediol is not in the range of the present invention.

[Table 2]

Figure 2:
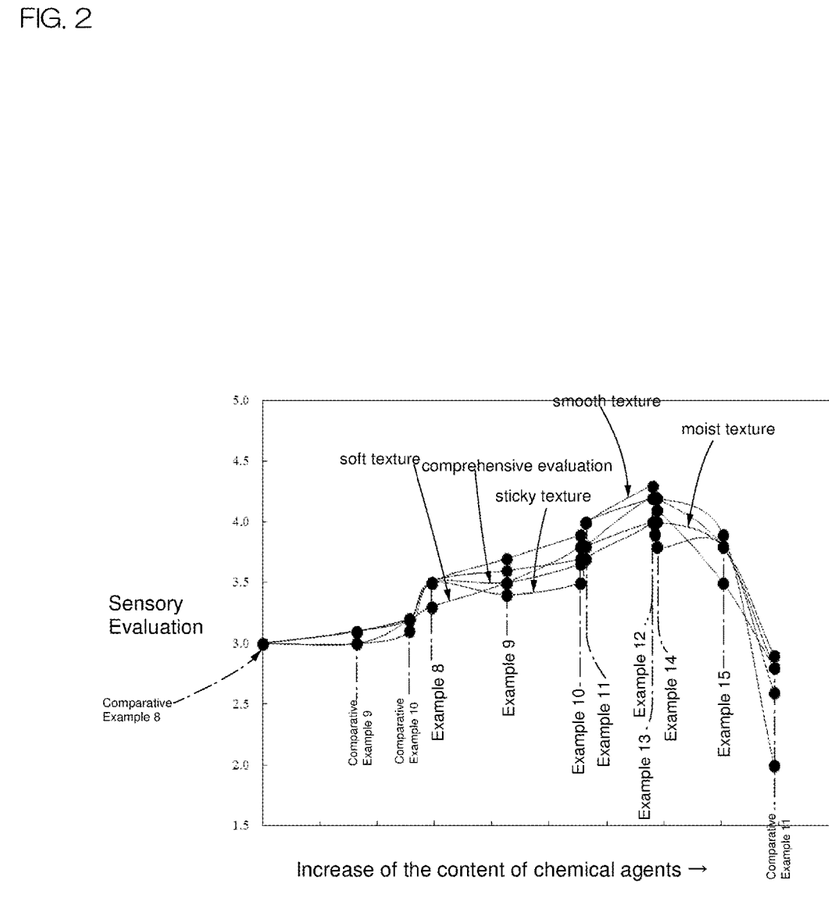
FIG. 2 is a graph showing the results of test examples according to an embodiment.

Table 2 mainly shows the test results of each sample in which the content of chemical agent was changed. The reference sample of sensory evaluation is a general-purpose one to which chemical agent is not applied (Comparative Example 8). In addition, the graph of the sensory evaluation results of Example 8 to Example 15 and Comparative Example 8 to Comparative Example 11 is shown in FIG. 2. As shown in Table 2 and FIG. 2, when the content of chemical agent is in the range of the present invention, remarkably excellent results were obtained in the evaluation items of "soft texture," "smooth texture," "moist texture" and "sticky texture" compared to those of the reference sample. Very remarkably high evaluation was obtained particularly in "smooth texture," "moist texture" and "sticky texture." From the above, it is found that when the content of chemical agent is in the range of the present invention, tissue paper which is "smooth and moist" and in which "stickiness" is not easily felt can be obtained. The evaluation of "soft texture" was also high. From Table 2, it can be further verified that when the content of chemical agent is lower or higher than the range of the present invention, the evaluation is not good even when the mass ratio of glycerin and 1,3-propanediol is in the range of the present invention.

Furthermore, when focusing on Comparative Example 12, remarkable results were not verified in a case where the total mass % of glycerin and 1,3-propanediol and the mass ratio of glycerin and 1,3-propanediol is not in the range of the present invention even when the total proportion of glycerin and 1,3-propanediol in chemical agent is in the range of the present invention.

CONCLUSION

From the above results of each test, tissue paper in which particularly both a "moist texture" and "smooth texture" are improved, a "moist texture" is retained and simultaneously "smooth texture" can be sufficiently felt can be obtained by adjusting the combined proportion of glycerin and 1,3-propanediol in chemical agent, the blending ratio of glycerin and 1,3-propanediol and the content of chemical agent to the range of the present invention. Furthermore, a "sticky texture" is limited and "soft texture" is also high. As described above, according to the present invention, the quality characteristics of tissue paper, "soft texture," "smooth texture," "moist texture" and "sticky texture" are excellent.

TABLE 1

| | | | Example 1 | Example 2 | Example 3 | Example 4 | Example 5 | Example 6 | Example 7 |
|---|---|---|---|---|---|---|---|---|---|
| Base paper making | Blended pulp ratio | NBKP:LBKP | 50:50 | 50:50 | 50:50 | 50:50 | 50:50 | 50:50 | 50:50 |
| | Crepe rate | % | 14.0 | 14.0 | 14.0 | 14.0 | 14.0 | 14.0 | 14.0 |
| | Softening agent | mass % | 0.6 | 0.6 | 0.6 | 0.6 | 0.6 | 0.6 | 0.6 |
| | Dry paper strengthening agent | mass % | 0.0 | 0.0 | 0.0 | 0.0 | 0.0 | 0.0 | 0.0 |
| | Wet paper strengthening agent | mass % | 1.2 | 1.2 | 1.2 | 1.2 | 1.2 | 1.2 | 1.2 |
| Chemicals application | Chemicals application | Yes or No | Yes | Yes | Yes | Yes | Yes | Yes | Yes |
| | Application method | | Gravure transfer | Gravure transfer | Gravure transfer | Gravure transfer | Gravure transfer | Gravure transfer | Gravure transfer |
| Moisturizer component | Moisturizing component Glycerin | mass % | 81.0 | 69.0 | 55.0 | 49.0 | 42.5 | 22.0 | 13.0 |
| | 1,3-Propanediol | mass % | 4.0 | 8.0 | 20.0 | 36.0 | 42.5 | 58.0 | 72.0 |
| | Sorbitol | mass % | 0.0 | 8.0 | 10.0 | 0.0 | 0.0 | 5.0 | 0.0 |
| | Softening agent Phosphate ester | mass % | 1.3 | 1.3 | 1.3 | 1.3 | 1.3 | 1.3 | 1.3 |
| | Oily component Liquid paraffin | mass % | 2.3 | 2.3 | 2.3 | 2.3 | 2.3 | 2.3 | 2.3 |
| | Hydrophilic polymer gelling agent (glucomannan) | mass % | 0.5 | 0.5 | 0.5 | 0.5 | 0.5 | 0.5 | 0.5 |
| | Emulsifier | mass % | 0.3 | 0.3 | 0.3 | 0.3 | 0.3 | 0.3 | 0.3 |
| | Preservative | mass % | 0.1 | 0.1 | 0.1 | 0.1 | 0.1 | 0.1 | 0.1 |
| | Defoamer | mass % | 0.05 | 0.05 | 0.05 | 0.05 | 0.05 | 0.05 | 0.05 |
| | Water (water content in chemical liquid) | mass % | 10.5 | 10.5 | 10.5 | 10.5 | 10.5 | 10.5 | 10.5 |
| | Total | mass % | 100.0 | 100.0 | 100.0 | 100.0 | 100.0 | 100.0 | 100.0 |
| | Glycerin + 1,3propanediol (in chemical) | mass % | 94.9 | 86.0 | 83.7 | 94.9 | 94.9 | 89.3 | 94.9 |
| | Mass ratio | (Glycerin):(1,3Propanediol) | 1:0.05 | 1:0.12 | 1:0.36 | 1:0.74 | 1:1 | 1:2.64 | 1:5.56 |
| Content of chemical agent and the like | Content rate of chemical agent | g/m2 | 6.8 | 6.7 | 6.9 | 6.7 | 6.6 | 6.8 | 6.9 |
| | Content of chemical agent (including water) | mass % | 25.0 | 25.0 | 25.0 | 25.0 | 25.0 | 25.0 | 25.0 |
| | Content rate of chemical agent (Absolute dry) | mass % | 22.4 | 22.4 | 22.4 | 22.4 | 22.4 | 22.4 | 22.4 |
| | Ratio of 1,3-propanediol in paper | mass % | 1.0 | 2.0 | 5.0 | 9.0 | 10.6 | 14.5 | 18.0 |
| Product quality | Base weight (1P) | g/m² | 17.0 | 16.8 | 17.3 | 16.8 | 16.6 | 17.0 | 17.2 |
| | Paper thickness (2P) | mm | 144 | 143 | 142 | 142 | 140 | 139 | 136 |
| | Density (2P) | g/cm³ | 0.24 | 0.23 | 0.24 | 0.24 | 0.24 | 0.24 | 0.25 |
| | Dry tensile strength (MD) 2P | cN/25 mm | 176 | 165 | 160 | 151 | 150 | 149 | 148 |
| | Dry tensile strength (CD) 2P | cN/25 mm | 62 | 61 | 58 | 55 | 53 | 51 | 53 |
| | Wet tensile strength (MD) 2P | cN/25 mm | 90 | 84 | 82 | 77 | 77 | 76 | 75 |
| | Wet tensile strength (CD) 2P | cN/25 mm | 42 | 43 | 41 | 50 | 42 | 40 | 39 |
| | Wet tensile strength (CD) 2P/Dry tensile strength (CD) 2P | | 0.68 | 0.70 | 0.71 | 0.91 | 0.79 | 0.78 | 0.74 |
| | Elongation rate (MD) | % | 11.6 | 11.2 | 11.1 | 11.0 | 11.3 | 10.5 | 10.8 |
| | Softness | cN/100 mm | 0.82 | 0.78 | 0.76 | 0.70 | 0.72 | 0.70 | 0.68 |
| | MMD (face) | 1/100 | 6.4 | 6.8 | 6.4 | 6.5 | 6.8 | 6.2 | 6.3 |
| | Product water content rate | mass % | 11.8 | 12.4 | 13.6 | 14.2 | 15.0 | 15.4 | 15.6 |
| Sensory evaluation | Soft texture | | 3.3 | 3.5 | 3.6 | 3.6 | 3.6 | 3.5 | 3.4 |
| | Smooth texture | | 3.5 | 3.7 | 4.2 | 4.3 | 4.4 | 4.2 | 3.9 |
| | Moist texture | | 3.5 | 3.6 | 4.0 | 4.0 | 4.0 | 3.9 | 3.7 |
| | Sticky texture | | 3.5 | 3.6 | 4.0 | 4.1 | 4.2 | 4.1 | 3.9 |
| | Comprehensive evaluation | | 3.5 | 3.6 | 4.0 | 3.9 | 4.0 | 4.0 | 3.8 |

TABLE 1-continued

| | | | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| Base paper making | Blended pulp ratio | NBKP:LBKP | 50:50 | 50:50 | 50:50 | 50:50 | 50:50 | 50:50 | 50:50 |
| | Crepe rate | % | 14.0 | 14.0 | 14.0 | 14.0 | 14.0 | 14.0 | 14.0 |
| | Softening agent | mass % | 0.6 | 0.6 | 0.6 | 0.6 | 0.6 | 0.6 | 0.6 |
| | Dry paper strengthening agent | mass % | 0.0 | 0.0 | 0.0 | 0.0 | 0.0 | 0.0 | 0.0 |
| | Wet paper strengthening agent | mass % | 1.2 | 1.2 | 1.2 | 1.2 | 1.2 | 1.2 | 1.2 |
| Chemicals application | Chemicals application | Yes or No | Yes | Yes | Yes | Yes | Yes | Yes | Yes |
| | Application method | | Gravure transfer | Gravure transfer | Gravure transfer | Gravure transfer | Gravure transfer | Gravure transfer | Gravure transfer |
| Moisturizer component | Moisturizing component Glycerin | mass % | 85.0 | 75.5 | 82.0 | 4.9 | 2.0 | 1.5 | 0.0 |
| | 1,3-Propanediol | mass % | 0.0 | 1.5 | 3.0 | 80.0 | 83.0 | 83.5 | 85.0 |
| | Sorbitol | mass % | 0.0 | 8.0 | 0.0 | 0.0 | 0.0 | 0.0 | 0.0 |
| | Softening agent Phosphate ester | mass % | 1.3 | 1.3 | 1.3 | 1.3 | 1.3 | 1.3 | 1.3 |
| | Oily component Liquid paraffin | mass % | 2.3 | 2.3 | 2.3 | 2.3 | 2.3 | 2.3 | 2.3 |
| | Hydrophilic polymer gelling agent (glucomannan) | mass % | 0.5 | 0.5 | 0.5 | 0.5 | 0.5 | 0.5 | 0.5 |
| | Emulsifier | mass % | 0.3 | 0.3 | 0.3 | 0.3 | 0.3 | 0.3 | 0.3 |
| | Preservative | mass % | 0.1 | 0.1 | 0.1 | 0.1 | 0.1 | 0.1 | 0.1 |
| | Defoamer | mass % | 0.05 | 0.05 | 0.05 | 0.05 | 0.05 | 0.05 | 0.05 |
| | Water (water content in chemical liquid) | mass % | 10.5 | 10.5 | 10.5 | 10.5 | 10.5 | 10.5 | 10.5 |
| | Total | mass % | 100.0 | 100.0 | 100.0 | 100.0 | 100.1 | 100.0 | 100.0 |
| | Glycerin + 1,3propanediol (in chemical) | mass % | 94.9 | 86.0 | 94.9 | 94.9 | 95.0 | 94.9 | 94.9 |
| | Mass ratio | (Glycerin):(1,3Propanediol) | 1:0 | 1:0.02 | 1:0.04 | 1:16.33 | 1:41.5 | 1:57.59 | 0:01 |
| Content of chemical agent and the like | Content rate of chemical agent | g/m2 | 6.8 | 7.0 | 6.9 | 6.9 | 6.8 | 6.8 | 7.0 |
| | Content of chemical agent (including water) | mass % | 25.0 | 25.0 | 25.0 | 25.0 | 25.0 | 25.0 | 25.0 |
| | Content rate of chemical agent (Absolute dry) | mass % | 22.4 | 22.4 | 22.4 | 22.4 | 22.4 | 22.4 | 22.4 |
| | Ratio of 1,3-propanediol in paper | mass % | 0.0 | 0.4 | 0.8 | 20.0 | 20.8 | 20.9 | 21.3 |
| Product quality | Base weight (1P) | g/m² | 16.9 | 17.5 | 17.3 | 17.2 | 17.1 | 17.0 | 17.4 |
| | Paper thickness (2P) | mm | 150 | 145 | 146 | 136 | 150 | 150 | 150 |
| | Density (2P) | g/cm³ | 0.23 | 0.24 | 0.24 | 0.25 | 0.23 | 0.23 | 0.23 |
| | Dry tensile strength (MD) 2P | cN/25 mm | 196 | 190 | 188 | 148 | 145 | 146 | 149 |
| | Dry tensile strength (CD) 2P | cN/25 mm | 67 | 66 | 65 | 53 | 52 | 50 | 50 |
| | Wet tensile strength (MD) 2P | cN/25 mm | 99 | 99 | 99 | 75 | 99 | 99 | 99 |
| | Wet tensile strength (CD) 2P | cN/25 mm | 45 | 43 | 41 | 39 | 40 | 42 | 40 |
| | Wet tensile strength (CD) 2P/Dry tensile strength (CD) 2P | | 0.67 | 0.65 | 0.63 | 0.74 | 0.77 | 0.84 | 0.80 |
| | Elongation rate (MD) | % | 12.0 | 12.2 | 11.8 | 10.8 | 10.4 | 10.3 | 10.0 |
| | Softness | cN/100 mm | 0.88 | 0.85 | 0.86 | 0.68 | 0.88 | 0.88 | 0.88 |
| | MMD (face) | 1/100 | 6.7 | 6.8 | 6.6 | 6.3 | 6.2 | 6.3 | 6.1 |
| | Product water content rate | mass % | 9.8 | 10.2 | 10.4 | 15.8 | 16.3 | 16.3 | 16.8 |
| Sensory evaluation | Soft texture | | 3.0 | 3.0 | 3.1 | 3.2 | 3.0 | 2.9 | 2.8 |
| | Smooth texture | | 3.0 | 3.0 | 3.1 | 3.5 | 3.2 | 3.0 | 3.1 |
| | Moist texture | | 3.0 | 3.0 | 3.1 | 3.5 | 3.0 | 3.1 | 3.0 |
| | Sticky texture | | 3.0 | 3.0 | 3.1 | 3.4 | 3.1 | 3.0 | 3.0 |
| | Comprehensive evaluation | | 3.0 | 3.0 | 3.1 | 3.4 | 3.1 | 3.0 | 3.0 |

TABLE 2

| | | | Example 8 | Example 9 | Example 10 | Example 11 | Example 12 | Example 13 | Example 14 | Example 15 | Comparative Example 8 | Comparative Example 9 | Comparative Example 10 | Comparative Example 11 | Comparative Example 12 |
|---|---|---|---|---|---|---|---|---|---|---|---|---|---|---|---|
| Base paper making | Blended pulp ratio | NBKP:LBKP | 50:50 | 50:50 | 50:50 | 50:50 | 50:50 | 50:50 | 50:50 | 50:50 | 50:50 | 50:50 | 50:50 | 50:50 | 50:50 |
| | Crepe rate | % | 14.0 | 14.0 | 14.0 | 14.0 | 14.0 | 14.0 | 14.0 | 14.0 | 14.0 | 14.0 | 14.0 | 14.0 | 14.0 |
| | Softening agent | mass % | 0.6 | 0.6 | 0.6 | 0.6 | 0.6 | 0.6 | 0.6 | 0.6 | 0.6 | 0.6 | 0.6 | 0.6 | 0.6 |
| | Dry paper strengthening agent | mass % | 0.0 | 0.0 | 0.0 | 0.0 | 0.0 | 0.0 | 0.0 | 0.0 | 0.0 | 0.0 | 0.0 | 0.0 | 0.0 |
| | Wet paper strengthening agent | mass % | 1.2 | 1.2 | 1.2 | 1.2 | 1.2 | 1.2 | 1.2 | 1.2 | 1.2 | 1.2 | 1.2 | 1.2 | 1.2 |
| Chemicals application | Chemicals application | Yes or No | Yes | Yes | Yes | Yes | Yes | Yes | Yes | Yes | Yes | Yes | Yes | Yes | Yes |
| | Application method | | Gravure transfer | Gravure transfer | Gravure transfer | Gravure transfer | Gravure transfer | Gravure transfer | Gravure transfer | Gravure transfer | — | Gravure transfer | Gravure transfer | Gravure transfer | Gravure transfer |
| Moisturizer component | Moisturizing component Glycerin | mass % | 42.5 | 42.5 | 48.9 | 34.4 | 42.5 | 24.9 | 12.9 | 18.4 | — | 72.9 | 74.9 | 12.9 | 8.9 |
| | 1,3-Propanediol | mass % | 42.5 | 42.5 | 36.0 | 42.5 | 42.5 | 60.0 | 72.0 | 66.5 | — | 12.0 | 10.0 | 72.0 | 76.0 |
| | Sorbitol | mass % | 0.0 | 0.0 | 0.0 | 8.0 | 0.0 | 0.0 | 0.0 | 0.0 | — | 0.0 | 0.0 | 0.0 | 0.0 |
| | Softening agent Phosphate ester | mass % | 1.3 | 1.3 | 1.3 | 1.3 | 1.3 | 1.3 | 1.3 | 1.3 | — | 1.3 | 1.3 | 1.3 | 1.3 |
| | Oily component Liquid paraffin | mass % | 2.3 | 2.3 | 2.3 | 2.3 | 2.3 | 2.3 | 2.3 | 2.3 | — | 2.3 | 2.3 | 2.3 | 2.3 |
| | Hydrophilic polymer gelling agent (glucomannan) | mass % | 0.5 | 0.5 | 0.5 | 0.5 | 0.5 | 0.5 | 0.5 | 0.5 | — | 0.5 | 0.5 | 0.5 | 0.5 |
| | Emulsifier | mass % | 0.3 | 0.3 | 0.3 | 0.3 | 0.3 | 0.3 | 0.3 | 0.3 | — | 0.3 | 0.3 | 0.3 | 0.3 |
| | Preservative | mass % | 0.1 | 0.1 | 0.1 | 0.1 | 0.1 | 0.1 | 0.1 | 0.1 | — | 0.1 | 0.1 | 0.1 | 0.1 |
| | Defoamer | mass % | 0.05 | 0.05 | 0.05 | 0.05 | 0.05 | 0.05 | 0.05 | 0.05 | — | 0.05 | 0.05 | 0.05 | 0.05 |
| | Water (water content in chemical liquid) | mass % | 10.5 | 10.5 | 10.5 | 10.5 | 10.5 | 10.5 | 10.5 | 10.5 | — | 10.5 | 10.5 | 10.5 | 10.5 |
| | Total | mass % | 100.0 | 100.0 | 100.0 | 100.0 | 100.0 | 100.0 | 100.0 | 100.0 | — | 100.0 | 100.0 | 100.0 | 100.0 |
| | Glycerin + 1,3propanediol (in chemical) | mass % | 94.9 | 94.9 | 94.9 | 85.9 | 94.9 | 94.9 | 94.9 | 94.9 | — | 94.9 | 94.9 | 94.9 | 94.9 |
| | Mass ratio | (Glycerin):(1,3Propanediol) | 1:1 | 1:1 | 1:0.74 | 1:1.24 | 1:1 | 1:2.41 | 1:5.58 | 1:3.61 | — | 1:0.16 | 1:0.13 | 1:5.58 | 1:8.54 |
| Content of chemical agent and the like | Content rate of chemical agent (including water) | g/m2 | 2.9 | 4.3 | 5.5 | 5.6 | 6.9 | 6.8 | 6.8 | 8.0 | — | 1.6 | 2.5 | 8.9 | 7.9 |
| | Content rate of chemical agent (Absolute dry) | mass % | 10.0 | 15.0 | 20.0 | 20.0 | 25.0 | 25.0 | 25.0 | 30.0 | — | 5.0 | 8.0 | 35.0 | 30.0 |
| | Ratio of 1,3-propanediol in paper | mass % | 9.0 | 13.4 | 17.9 | 17.9 | 22.4 | 22.4 | 22.4 | 26.9 | — | 4.5 | 7.2 | 31.3 | 26.9 |
| | | mass % | 4.3 | 6.4 | 7.2 | 8.5 | 10.6 | 15.0 | 18.0 | 20.0 | — | 0.6 | 0.8 | 25.2 | 22.8 |
| Product quality | Base weight (1P) | g/m2 | 16.2 | 16.3 | 16.6 | 16.9 | 17.2 | 17.0 | 17.1 | 17.4 | 15.2 | 17.2 | 17.2 | 17.2 | 17.2 |
| | Paper thickness (2P) | mm | 152 | 156 | 155 | 150 | 152 | 150 | 150 | 150 | 153 | 145 | 145 | 145 | 145 |
| | Density (2P) | g/cm3 | 0.21 | 0.21 | 0.21 | 0.23 | 0.23 | 0.23 | 0.23 | 0.23 | 0.20 | 0.24 | 0.24 | 0.24 | 0.24 |
| | Dry tensile strength (MD) 2P | cN/25 mm | 210 | 226 | 230 | 200 | 210 | 200 | 200 | 200 | 196 | 196 | 196 | 196 | 196 |
| | Dry tensile strength (CD) 2P | cN/25 mm | 53 | 53 | 53 | 53 | 53 | 53 | 53 | 53 | 67 | 67 | 67 | 67 | 67 |
| | Wet tensile strength (MD) 2P | cN/25 mm | 122 | 122 | 122 | 98 | 99 | 100 | 82 | 82 | 99 | 99 | 99 | 98 | 99 |
| | Wet tensile strength (CD) 2P | cN/25 mm | 58 | 56 | 58 | 56 | 55 | 56 | 51 | 51 | 45 | 45 | 45 | 46 | 45 |
| | Wet tensile strength (CD) 2P/Dry tensile strength (CD) 2P | | 1.09 | 1.06 | 1.09 | 1.06 | 1.04 | 1.06 | 0.96 | 0.96 | 0.67 | 0.67 | 0.67 | 0.69 | 0.67 |
| | Elongation rate (MD) | % | 9.5 | 10.2 | 10.4 | 9.0 | 9.5 | 9.0 | 9.5 | 9.5 | 9.9 | 9.9 | 9.9 | 8.8 | 9.9 |
| | Softness | cN/100 mm | 0.78 | 0.80 | 0.82 | 0.72 | 0.78 | 0.72 | 0.72 | 0.72 | 0.85 | 0.85 | 0.85 | 0.85 | 0.85 |
| | MMD (face) | 1/100 | 6.4 | 6.7 | 6.5 | 6.5 | 6.4 | 6.5 | 6.5 | 6.5 | 6.6 | 6.6 | 6.6 | 6.6 | 6.6 |
| | Product water content rate | % | 11.3 | 12.2 | 13.4 | 14.5 | 15.0 | 15.0 | 14.8 | 15.9 | 16.5 | 16.5 | 16.5 | 17.0 | 16.5 |
| Sensor evaluation | Soft texture | | 3.3 | 3.5 | 3.8 | 4.0 | 4.2 | 4.2 | 4.2 | 3.8 | 3.0 | 3.1 | 3.2 | 2.8 | 2.9 |
| | Smooth texture | | 3.5 | 3.7 | 3.9 | 4.0 | 4.0 | 4.3 | 4.2 | 3.9 | 3.0 | 3.1 | 3.2 | 2.0 | 2.5 |
| | Moist texture | | 3.5 | 3.6 | 3.7 | 3.8 | 3.8 | 4.0 | 3.9 | 3.8 | 3.0 | 3.0 | 3.1 | 2.9 | 2.8 |
| | Sticky texture | | 3.5 | 3.4 | 3.5 | 3.7 | 4.1 | 4.2 | 4.2 | 3.8 | 3.0 | 3.0 | 3.2 | 2.6 | 2.8 |
| | Comprehensive evaluation | | 3.5 | 3.6 | 3.7 | 3.8 | 4.1 | 4.2 | 3.9 | 3.5 | 3.0 | 3.0 | 3.2 | 2.8 | 2.8 |

The invention claimed is:

1. A 2-ply tissue paper, wherein
a basis weight per ply is 15 to 18 g/m$^2$,
the 2-ply paper thickness is 135 to 160μm, and the 2-ply tissue paper contains 2.9 g/m$^2$ or more and 8.0 g/m$^2$ or less of chemical agents which contains glycerin and 1,3- propanediol, wherein glycerin and 1,3-propanediol weigh between 83.7 mass % or more and 94.9 or less mass % in a total amount of the chemical agents, wherein the blending ratio of 1,3-propanediol to glycerin is above 1: 0.04 and 1: 5.58 or less.

2. A 2-ply tissue paper, wherein
a basis weight per ply is 16.2 g/m$^2$ or more and 17.4 g/m$^2$ or less,
the 2-ply paper thickness is 136 pm or more and 156 pm or less, and the 2-ply tissue paper contains 2.9 g/m$^2$ or more and 8.0 g/m$^2$ or less of chemical agents which contain glycerin and 1,3- propanediol, wherein glycerin and 1,3-propanediol weigh between 83.7 mass % or more and 94.9 or less mass % in a total amount of the chemical agents, wherein the blending ratio of 1,3-propanediol to glycerin is above 1: 0.04 and 1: 5.58 or less.

3. The 2-ply tissue paper according to claim 1, wherein
the 2-ply dry tensile strength in the CD direction is 51 cN/25 mm or more and 62cN/25mm or less,
the 2-ply wet tensile strength in the CD direction is 39 cN/25 mm or more and 58cN/25mm or less, and
the ratio of the 2-ply wet tensile strength in the CD direction to the 2-ply dry tensile strength in the CD direction is 0.68 or more.

* * * * *